United States Patent [19]

Hsieh

[11] Patent Number: 4,833,078

[45] Date of Patent: * May 23, 1989

[54] SEMI-CONTINUOUS FERMENTATION PROCESS FOR AROMATIC HYDROCARBON BIOCONVERSION

[75] Inventor: Jih-Han Hsieh, Parsippany, N.J.

[73] Assignee: Celgene Corporation, Warren, N.J.

[*] Notice: The portion of the term of this patent subsequent to Oct. 30, 2001 has been disclaimed.

[21] Appl. No.: 623,604

[22] Filed: Jun. 22, 1984

[51] Int. Cl.$^4$ .......................... C12P 7/44; C12R 1/40; C12N 1/20; C12M 1/12

[52] U.S. Cl. .................................... 435/142; 435/813; 435/253.3; 435/877; 435/311

[58] Field of Search ............... 435/311, 104, 136, 813, 435/877, 142

[56] References Cited

U.S. PATENT DOCUMENTS

| | | | |
|---|---|---|---|
| 2,822,319 | 2/1958 | Monod | 435/813 |
| 4,278,764 | 7/1981 | Rottigni et al. | 435/813 |
| 4,310,629 | 1/1982 | Muller et al. | 435/813 |
| 4,328,308 | 5/1982 | Weisrock | 435/104 |
| 4,355,107 | 10/1982 | Maxwell | 435/142 |
| 4,399,221 | 8/1983 | Schneider et al. | 435/101 |
| 4,440,853 | 4/1984 | Michaels et al. | 435/813 |
| 4,443,544 | 4/1984 | Rogers et al. | 435/813 |
| 4,480,034 | 10/1984 | Hsieh | 435/136 |
| 4,535,059 | 8/1985 | Hsieh et al. | 435/136 |

Primary Examiner—J. E. Tarcza
Attorney, Agent, or Firm—Bruce M. Collins

[57] ABSTRACT

This invention provides a semi-continuous fermentation process which is operated in a repeated fed-batch mode to maintain cell bioconversion productivity at a high level without product inhibition of enzymatic activity. The process is illustrated by the bioconversion of toluene or catechol via the ortho pathway to muconic acid which accumulates in the fermentation medium in a quantity up to about 50 grams per liter.

7 Claims, No Drawings

SEMI-CONTINUOUS FERMENTATION PROCESS FOR AROMATIC HYDROCARBON BIOCONVERSION

BACKGROUND OF THE INVENTION

Carboxylic acids are important high volume commodities in the chemical industry. For example, it is estimated that the 1982 worldwide capacity for adipic acid is about five billion pounds.

Adipic acid is produced by oxidation of cyclohexane or cyclohexanol with nitric acid in the presence of a vanadium-copper catalyst. Other methods of synthesizing adipic acid include 1,3-butadiene carbonylation with carbon monoxide followed by hydrolysis; methyl acrylate dimerization; and 1,4-butanediol carbonylation.

The surge of recent biotechnical advances has increased interest in the potential application of bioconversion systems for the production of high volume chemicals such as adipic acid and other carboxylic acids and commercially established commodities.

One prospective new method of synthesizing a carboxylic acid such as adipic acid is by the hydrogenation of muconic acid, which is a diolefinically unsaturated adipic acid derivative:

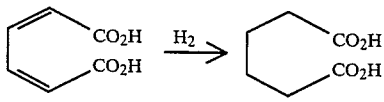

A potentially convenient source of muconic acid is by the microbiological oxidation of various hydrocarbon substrates. Microbiological oxidation of hydrocarbons is reviewed in Applied Microbiology, 9(5), 383(1961) and in "Advances in Enzymology", 27, 469–546(1965) by Interscience Publishers.

The Journal of Biological Chemistry, 241(16), 3776 (1966) reports the conversion of catechol and protocatechuate to β-ketoadipate by *Pseudomonas putida*. The conversion of catechol proceeds by the ortho pathway via a muconic acid intermediate:

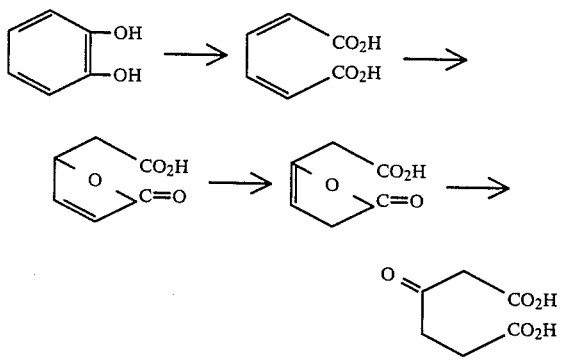

The chemical structures illustrated in the reaction scheme are catechol, muconic acid, muconolactone, β-ketoadipate enollactone and β-ketoadipate, respectively.

In the Journal Of Bacteriology, 134, 756(1978) there is reported a study of the ubiquity of plasmids in coding for toluene and xylene metabolism in soil bacteria. One of the mutant strains of *Pseudomonas putida* isolated had the ability to metabolize toluene via benzyl alcohol, benzaldehyde, benzoic acid and catechol by the ortho pathway through β-ketoadipate to a biomass and carbon dioxide.

The enzymes functioning in the toluene metabolism by the ortho pathway included toluene mono-oxygenase, benzyl alcohol dehydrogenase, benzaldehyde dehydrogenase, benzoate oxygenase, dihydrodihydroxybenzoate dehydrogenase, catechol 1,2-oxygenase and muconate lactoning enzyme. The subsequently formed β-ketoadipate was further assimilated to biomass and carbon dioxide. The mutant strains that metabolized toluene via the ortho pathway did not accumulate muconic acid, since the said muconic acid metabolite was further transformed in the presence of muconate lactonizing enzyme.

No known naturally occurring microorganisms (e.g., *Pseudomonas putida*) are known that metabolize an aromatic hydrocarbon substrate such as toluene by the ortho pathway via muconic acid and β-ketoadipate. Wild strains metabolize aromatic hydrocarbon substrates by the meta pathway via 2-hydroxymuconic semialdehyde instead of a muconic acid intermediate. Catechol 2,3-oxygenase is functional rather than catechol 1,2-oxygenase.

Thus, the potential of microbiological oxidation of toluene as a convenient source of muconic acid requires the construction of mutant strains of microorganisms which (1) metabolize toluene by means of the ortho pathway, and (2) allow the accumulation of muconic acid without further assimilation.

The said construction of the desirable mutant strains recently has been achieved, as exemplified by *Pseudomonas putida* Biotype A strain ATCC No. 31916.

As a consequence of the prospect of large scale bioconversion systems for production of carboxylic acid type compounds from lower cost hydrocarbon substrates, the problems of fermentation system stability, effective biocatalyst activity and consequential bioconversion product formation and accumulation, and of efficient recovery of extracellular bioconversion products contained in fermentation culture media are of increasing significance. The product inhibition of enzymatic activity by an accumulated carboxylic acid metabolite in a fermentation medium is a serious obstacle to efficient production of the carboxylic acid metabolite as a desired product of the process.

Accordingly, it is an object of this invention to provide a bioconversion process for converting a non-growth aromatic hydrocarbon to an extracellular accumulated quantity of carboxylic acid metabolite with little or no product inhibition of enzymatic activity.

It is a further object of this invention to provide a semi-continuous fermentation process for bio-oxidation of toluene or catechol via the ortho pathway to a high concentration of extracellular accumulated muconic acid with essentially no product inhibition of enzymatic activity, and to provide for the recovery of the muconic acid product.

Other objects and advantages of the present invention shall become apparent from the accompanying description and examples.

DESCRIPTION OF THE INVENTION

One or more objects of the present invention are accomplished by the provision of a semi-continuous bioconversion process operating in a fed-batch mode which comprises (1) continuously feeding a non-growth aromatic hydrocarbon substrate, an aqueous nutrient stream and molecular oxygen into a fermentation zone containing a microorganism which bio-oxidizes the aromatic hydrocarbon to an extracellular water-soluble carboxylic acid product having a molecular weight less than about 1000; (2) maintaining the fermentation conditions until the concentration of the carboxylic acid product in the fermentation medium has reached a level of at least about 5 grams per liter of fermentation medium with little or no product inhibition of enzymatic activity, then stopping the input of aromatic hydrocarbon and aqueous nutrient stream into the fermentation zone and continuing the input of molecular oxygen; (3) withdrawing the whole cell-containing fermentation broth from the fermentation zone and passing the withdrawn fermentation broth through a cross-flow membrane filtration zone, then recovering a whole cell-containing retentate stream and a cell-free product-containing permeate stream from the filtration zone and recycling the retentate stream to the fermentation zone; (4) charging the fermentation zone with a volume of fresh aqueous nutrient medium to replace the withdrawn volume of permeate fermentation broth, and resuming the fermentation conditions by recommencing the continuous feed of non-growth aromatic hydrocarbon and aqueous nutrient stream into the fermentation zone to produce carboxylic acid product up to a concentration of at least about 5 grams per liter of fermentation medium without product inhibition of enzymatic activity; (5) withdrawing the whole cell-containing fermentation broth from the fermentation zone and passing the withdrawn fermentation broth through a cross-flow membrane filtration zone, then recovering a whole cell-containing retentate stream and a cell-free product-containing permeate stream from the filtration zone and recycling the retentate stream to the fermentation zone; and (6) recovering carboxylic acid product from the cell-free permeate streams, and optionally repeating the fed-batch cycle to produce additional carboxylic acid product.

The invention process generally is applicable for the production and recovery of carboxylic acid and other metabolites which accumulate as extracellular products. Illustrative of carboxylic acid metabolites which can be produced and separated and recovered from fermentation media include aliphatic and aromatic carboxylic acids such as pyruvic acid, butanoic acid, hexanoic acid, succinic acid, glutaric acid, ketoadipic acid, muconic acid, $\alpha\alpha$-dimethylmuconic acid, $\beta$-carboxymuconic acid, benzoic acid, alkylbenzoic acid, salicylic acid, phenylacetic acid, phenylpyruvic acid, nicotinic acid, and the like.

The cross-flow membrane filtration system employed can be selected from the various hollow fiber, tube, plate and frame, and spiral wound types of modular ultra filtration systems which have been developed and are available as commercial products.

Romicon (Woburn, Mass.) markets polysulfone membrane hollow fiber or tube ultra filtration systems. Millipore (Bedford, Mass.) has available plate and frame cassette and spiral wound modular ultra filtration systems, with cellulosic polymer, polysulfone and polyimide types of membranes. Dorr-Oliver (Westport, Conn.) sells a plate and frame ultrafiltration system with a polysulfone type of membrane. Other commercially available cross-flow filtration systems are produced by companies such as Osmonics (Minnetonka, Minn.), DDS (Nakskov, Denmark), Abcor (Wilmington, Mass.), Nuclearpore (Calif.) and N-D-A (New York).

In a preferred embodiment the present invention provides a semi-continuous bioconversion process operating in a fed-batch mode which comprises (1) continuously feeding a toluene non-growth substrate, an aqueous nutrient stream and molecular oxygen into a fermentation zone containing a microorganism which bio-oxidizes the toluene by the ortho pathway to extracellular muconic acid product; (2) maintaining the fermentation conditions until the concentration of the muconic acid product in the fermentation medium has reached a level of at least about 15 grams per liter of fermentation medium with essentially no product inhibition of enzymatic activity, then stopping the input of toluene and aqueous nutrient stream into the fermentation zone and continuing the input of molecular oxygen; (3) withdrawing the whole cell-containing fermentation broth from the fermentation zone and passing the withdrawn fermentation broth through a cross-flow membrane filtration zone, then recovering a whole cell-containing retentate stream and a cell-free product-containing permeate stream from the filtration zone and recycling the retentate stream to the fermentation zone; (4) charging the fermentation zone with a volume of fresh aqueous nutrient medium to replace the withdrawn volume of permeate fermentation broth, and resuming the fermentation conditions by recommencing the continuous feed of toluene and aqueous nutrient stream into the fermentation zone to produce muconic acid product up to a concentration of at least about 15 grams per liter of fermentation medium without product inhibition of enzymatic activity; (5) withdrawing the whole cell-containing fermentation broth from the fermentation zone and passing the withdrawn fermentation broth through a cross-flow membrane filtration zone, then recovering a whole cell-containing retentate stream and a cell-free product-containing permeate stream from the filtration zone and recycling the retentate stream to the fermentation zone; and (6) recovering muconic acid product from the cell-free permeate streams, and optionally repeating the fed-batch cycle to produce additional muconic acid product.

The toluene feed stream can be partially or completely replaced by benzyl alcohol, benzaldehyde, benzoic acid, catechol, or mixtures thereof. Each compound is capable of quantitative bioconversion to accumulated extracellular muconic acid.

The term "nutrient stream" or "nutrient medium" as employed herein refers to an aqueous solution of inorganic and organic compounds which provide carbon, nitrogen, sulfur, phosphorus, iron, magnesium, and other elements essential for cell growth and viability. Typical nutrient formulations are illustrated in the Examples.

The term "product inhibition" as employed herein refers to the inhibition of enzymatic activity and the suppression of enzyme induction caused by the presence of an accumulated quantity of a specific metabolite product.

The term "non-growth substrate" as employed herein refers to an organic carbon source which is bio-oxidized to a metabolite product, but not to biomass for cell growth.

The term "nutrient-limited" as employed herein refers to an essential fermentation parameter with respect to cell stability, as more fully disclosed in copending patent application Ser. No. 483,796, filed Apr. 11 1983 (incorporated by reference).

In a continuous fermentation system for cultivation of microorganisms, "growth nutrient-limitation" is necessary in order to achieve a "steady state". i.e., a constant level of cell concentration in a continuous flow reactor with a defined medium composition. The nutrient can be growth carbon, nitrogen, phosphate, sulfate, potassium, magnesium or any other growth-requiring trace metals, and/or oxygen in the case of aerobic fermentation.

The theory and practice of "nutrient-limitation" effects in fermentation systems is elaborated in the literature and in a number of standard textbooks such as Fermentation And Enzyme Technology (John Wiley & Sons, New York, 1979).

As indicated in the literature, conventional nutrient-limitation is primarily a technique to achieve steady state continuous fermentation and to study various yield and maintenance factors of cell mass with respect to various nutrients for cell growth. For the production of conventional fermentation products, such as ethanol, citric acid, lactic acid, acetic acid, and the like (primary metabolites), or antibiotics, microbial toxins, and the like (secondary metabolites) in a continuous flow reactor, nutrient-limitation can also be used to achieve steady state product formation. However, this type of nutrient-limitation has little or no effect on the stability of cells, i.e., the maintenance of the production and productivity level of a specific metabolite.

For a *Pseudomonas putida* Biotype A strain ATCC No. 31916 type of mutant strain, the cells grow on a preferred growth carbon and energy source (glucose, succinate or acetate) and convert a non-growth carbon substrate (e.g., toluene) to a metabolite product (e.g., muconic acid). The mutant strain prefers not to grow on toluene as a carbon source. However, in the presence of toluene and other nutrients over a period of about 3-4 days (24-30 generations), the mutant strain population has the tendency to "revert", i.e., exhibit the ability to grow on toluene again. Initially a small population of the cells reverts, and eventually the majority of the cell population reverts. This reversion problem is unique for these genetically manipulated microorganisms in bioconversion systems.

The application of nutrient-limitation to suppress this reversion phenomenon in bioconversion systems is novel. Thus, for microbial bioconversion processes, the nutrient-limitation aspect can be applied not only to achieve steady state production of cells and product, but also to improve the stability of cells.

For actively growing cells, the growth carbon can be limited to reduce catabolite repression and to increase the level of enzyme induction. Under nitrogen or phosphate or other nutrient-limited conditions, the cell growth is restricted, with the result that the cells selectively grow on a preferred carbon source, such as glucose, succinate or acetate, instead of growing on toluene or other non-growth carbon source. Consequently, the stability of a *P. putida* type of mutant strain is improved. This growth state can be found in continuous fermentation (chemostat) and in the early stage of repeated fed-batch fermentations.

For resting or non-growing cells under nutrient limitation, a present invention mutant strain, after proper induction to induce enzymes and in the absence of a growth nutrient, converts toluene to muconic acid and obtains energy from the reaction for cell maintenance, and concomitantly achieves cell stability. This situation can be found in the stationary growth phase (or later period) of a fed-batch fermentation, and in the concentrated cells of a continuous or semi-continuous with cell recycle fermentations.

It has been found that in order to achieve higher reactor productivity for muconic acid production the excess energy generated by the bioconversion needs to be removed. During a continuous or semi-continuous fermentation with cell recycle, a minimal amount of growth carbon and other nutrients is required for maintenance, and for growth as an energy sink to remove the excess energy generated.

In the practice of a present invention process embodiment, the carboxylic acid product can be recovered from a cell-free permeate stream by any technique suitable for isolating an organic carboxylic acid solute from an aqueous medium. Illustrative of a procedure for product recovery, a permeate stream containing soluble muconate salt (e.g., ammonium muconate) is acidified with a reagent such as sulfuric acid or phosphoric acid to convert the muconate salt to its free acid form. Under the acidic conditions (e.g., a pH of less than about 3) the muconic acid product precipitates out of solution (solubility of less than 0.02 weight percent). It is readily separated from the aqueous fermentation medium by As noted in the Background Of The Invention section above, the microbiological oxidation of toluene to accumulated muconic acid requires the construction of mutant strains of microorganisms, e.g., as exemplified by *Pseudomonas putida* Biotype A strain ATCC 31916.

This type of mutant strain can be provided by a process for microorganism construction which comprises (1) culturing microorganism species selectively to provide strain A1 which metabolizes toluene by the ortho pathway via catechol to muconic acid, and which subsequently metabolizes the resultant muconic acid via β-ketoadipate to biomass and carbon dioxide; (2) continuously and selectively culturing strain A1 for rapid growth on toluene as the sole source of carbon to provide strain A2; (3) culturing strain A2 in selective enrichment cycles in a medium containing benzoate as the sole source of carbon and containing an antibiotic which kills only growing cells; (4) harvesting the strain A2 cells and diluting and culturing the cells in media containing a non-selective carbon source; (5) plating the strain A2 cells on a nutrient medium containing a limiting amount of a non-selective carbon source and excess benzoate; (6) isolating cells from single small colonies, and culturing the cell isolates and selecting a strain A3, wherein strain A3 converts toluene to muconic acid and lacks active muconate lactonizing enzyme.

The starting microorganism can be any organism capable of growth on toluene or catechol and which possesses a catechol 1,2-oxygenase, e.g., a Pseudomonad. A variety of naturally occurring organisms have these traits including some members of the species *Pseudomonas putida, Pseudomonas aeruginosa, Pseudomonas fluorescens;* some members of the genera *Azotobacter* and *Nocardia;* and a number of unclassified fungi (both molds and yeasts).

The preferred constructed microorganisms are those described in U.S. Pat. No. 4,355,107, which possess a novel combination of enzymes which include (1) dihydrodihydroxybenzoate dehydrogenase; and (2) catechol 1,2-oxygenase with activity that is not inhibited in the presence of a low level (e.g., less than about five grams/liter) of muconic acid in a growth Illustrative of suitable microorganisms are constructed strains of fluorescent Pseudomonads each of which has the following characteristics:

(a) possesses catechol 1,2-oxygenase enzyme with activity that is not inhibited in the presence of a low level of muconic acid in a growth medium;

(b) lacks active catechol 2,3-oxygenase (c) lacks active muconate lactonizing enzyme; and (d) cells are rod shaped, vigorously motile and polarly flagellated.

Employing one of the constructed microorganisms described above for the present invention production of muconic acid from toluene, the rate of toluene conversion typically is about 0.3–1.2 gram of muconic acid produced per dry weight gram of cells per hour. The conversion of toluene proceeds readily at a dry weight cell concentration of 4–8 grams per liter, with a resultant muconic acid production rate of about 1.0–2.4 grams per liter of fermentation reactor working volume per hour.

Under optimal conditions, the muconic acid accumulation limit can approach up to about 50 grams of muconic acid per liter of fermentation medium. The microbiological oxidation step of the present invention process normally is conducted at ambient temperatures up to about 35° C.

The present invention semi-continuous process with a repeated fed-batch mode of operation is an alternative to a comparable type of bioconversion system which is operated continuously.

The present invention process has operational advantages for large scale operation as compared to a continuous type process at comparable volumetric reactor productivity. Equipment investment and operating costs are less, there is more effective use of ultra filtration modules, and product concentration in the product stream is higher and the product recovery cost is lower.

In the practice of the present invention process, reactor productivity (STY) is optimized by the achievement of high cell (biocatalyst) concentration, while maintaining high cell specific productivity.

This balance of advantages is not characteristic of either a batch or continuous mode of bioconversion operation. In conventional batch or fed-batch operations the biocatalysts are discarded after each batch resulting in higher production cost and the time required for reactor clean-up and start-up (inoculation) resulting in the loss of reactor productivity. In the continuous fermentation system, the whole cells are in constant contact with a high concentration of accumulated metabolite product, with a concomitant risk of product inhibition of enzymatic activity and suppression of enzyme induction.

The following examples are further illustrative of the present invention. The components and specific ingredients are presented as being typical, and various modifications can be derived in view of the foregoing disclosure within the scope of the invention.

For cultivation, carbon sources such as glucose, succinate or acetate are added aseptically prior to inoculation. Incubation conditions are in 250 ml shake flasks. Shaking is in a rotary shaker with temperature controlled at 28° C.

Growth is typically measured by determining the turbidity of the cell suspension in a Klett-Summerson Colorimeter using the #66 red filter. One Klett unit is equivalent to $3 \times 10^6$ cells per ml or 17.5 mg wet weight per liter or 3.52 mg dry weight per liter. Muconic acid salt is measured at 257 nm with a U.V. spectrophometer or monitored with a high performance liquid chromatograph.

Cultures are stored under liquid nitrogen.

EXAMPLE I

This Example illustrates the construction of a strain of microorganism which oxidizes toluene via the ortho (8-ketoadipate) pathway.

A series of mutants which metabolize toluene through the ortho pathway is constructed by first blocking the meta pathway and then isolating phenotypic revertants which have reacquired the ability to grow on benzoate. Strains possessing a meta pathway block are isolated after penicillin plus D-cycloserine enrichment for organisms which fail to grow on benzoate. Some isolates are then spotted into agar plates and incubated in the presence of toluene. Virtually all isolates revert to growth on toluene. The plates are sprayed with 10 mM catechol and approximately 25% of the revertants are found not to produce 2-hydroxymuconic semialdehyde. None of the colorless revertants are found to possess an active catechol 2,3-oxygenase following induction with toluene.

It has been shown by Worsey and Williams, J. Bacteriol. 130, 1149 (1977) that growth on benzoate tends to cure a population of its TOL plasmid because the ortho pathway supports a higher growth rate. Since toluate can only be metabolized via the meta pathway, an alternative way to cure a population of its TOL plasmid is to use the penicillin plus D-cycloserine procedure to enrich for cells unable to grow on toluate.

Both these techniques are used in succession followed by counter-selection for growth on toluene. A strain designated MW 1200 is first cultured on toluene. A small portion (0.05 ml) of this culture is transferred to 50 ml of benzoate medium. After growth on benzoate the cells are transferred to toluate and incubated for approximately one hour. Penicillin and D-cycloserine are then added as described above and the incubation is continued for four to six hours. Cells are harvested, washed and transferred to a toluene containing medium.

After growth on toluene the cells are plated on benzoate agar and incubated for 48 hours, and a number of large colonies and a few small colonies are formed. After spraying with catechol it is found that all of the small colonies turn yellow (indicating the presence of the meta pathway) but none of the large colonies do. Large colonies are picked and cultured and it is found that following growth on toluene, these strains contain no functional 2,3-oxygenase but are fully induced for the 1,2-oxygenase. These strains metabolized toluene by the ortho pathway. One isolate, designated MW 1210, is employed in Example II.

EXAMPLE II

This Example illustrates the construction of a *Pseudomonas putida* Biotype A strain ATCC No. 31916 type of mutant strain in accordance with the procedure described in U.S. Pat. No. 4,355,107.

Strain MW 1210 of Example I is subjected to continuous cultivation with toluene as the sole source of carbon. Initially a dilution rate of 0.15 hours$^{-1}$ is employed. After the culture had stabilized, the dilution rate is increased successively to 0.25 hour$^{-1}$, 0.34 hour$^{-1}$, and 0.46 hour$^{-1}$. An isolate is made from the cells which dominates the culture at this latter dilution rate. This strain is then used to construct a strain which accumulates muconic acid to greater than one gram per liter.

The above strain is cultured overnight in liquid medium on toluene as the sole source of carbon, then benzoate is added to a level of 5 mM and the incubation is continued for approximately 1 hour. Penicillin G and D-cycloserine are added at concentrations of 12 and 0.1 mg/ml respectively. The antibiotic incubation is continued for approximately 5 hours. The cells are then harvested by centrifugation and washed twice with sterile de-ionized water. An aliquot of these cells is transferred to fresh medium containing 0.5 mM p-hydroxybenzoate as a sole source of carbon, and the medium is incubated overnight. The procedure is repeated starting with induction with benzoate.

After 6 cycles those cells present in the culture after overnight growth on p-hydroxybenzoate are diluted and plated on an agar medium containing 0.5 mM succinate and 5.0 mM benzoate as sole sources of carbon. After 36 hours incubation the plate shows a mixture of large and small colonies. Cells from a number of small colonies are cultured in liquid medium, induced with toluene and tested for their ability to accumulate muconic acid. Isolate strains which accumulate muconic acid are identified.

One isolate, designated MW 1211.1, is employed in Examples III-IV.

EXAMPLE III

This Example illustrates a semi-continuous (repeated fed-batch) fermentation process for the production of muconic acid in accordance with the present invention.

A. Inoculum Preparation

A *Pseudomonas putida* Biotype A MW 1211.1 (ATCC No. 31916) mutant strain culture, stored frozen (regular "NO" medium aqueous culture in a polypropylene culture vial stored in liquid nitrogen) is thawed and transferred (1-1.5 ml) to a 250 ml shake flask containing 50 ml of regular "NO" medium (Table) with 20 mM of sodium succinate as a growth carbon source, and incubated at 30° C., 250 rpm for 16 hours to a turbidity of 180-220 klett units. (One klett unit is equivalent to 0.00352 g dry cell/liter broth or $3 \times 10^6$ cells/ml broth). Three shake flasks (150 ml inoculum) are inoculated aseptically to a 16 liter steam sterilizable fermentor (New Brunswick Scientific, Model SF116) containing 11.5 liter LP-1 medium (Table) with 20 mM of sodium acetate to initiate fermentation. The medium and the fermentor are sterilized for at least 30 minutes at 121° C. and 15 psig. After sterilization, the medium pH is adjusted to 6.9 with 5N NaOH solution.

B. Enzyme Induction

After the inoculation, toluene is supplied to the fermentation medium in vapor phase via air (filter sterilized, inlet pressure 20 psig) stripping at an air-toluene vapor flow rate of 125 cc/min. The fermentation temperature is controlled at 30° C., the pH at 6.9 with 10 M $NH_4OH$ and 1 M $H_2SO_4$ solutions, the dissolved oxygen at 30 to 90% saturation with 600 rpm agitation and 5-6 liter/minute aeration (or approximately 0.5 VVM, volume of air/volume of fermentation broth/minute, inlet air pressure 20 psig). Pluronic L61 polyol (BASF) is used as an anti-foam agent.

As the turbidity of the fermentation medium reaches 90-110 klett units (about 9-12 hours after inoculation), an aqueous solution containing 10 weight percent acetic acid, 0.114 weight percent $Na_2HPO_4$ and 0.218 weight percent $KH_2PO_4$ is added to the fermentation medium at a rate of 0.4 ml/minute. The air-toluene vapor rate is increased to 250 cc/minute and then increased to 500 cc/minute as the broth turbidity reaches 250 kletts.

C. Semi-Continuous (Repeated Fed-Batch) Fermentation

The air-toluene vapor rate is eventually increased to 750 cc/minute as the turbidity reaches 450-550 klett units. The fed-batch mode of fermentation is continued for 32-36 hours until a muconic acid product concentration of 15 g/l is reached.

The fermentation broth is passed through a Romicon hollow tube cross-flow ultrafilter (polysulfone membrane, PM-100, MW 100,000 cutoff) to concentrate and to recycle the cells (biocatalyst) back to the fermentor. A cell-free fermentation broth (about 9 liters) containing high muconic acid concentration is recovered as a separate stream from the ultrafilter. Fresh sterilized fermentation medium LP-1 (Table) is aseptically added to the fermentor to a total fermentation volume of 12 liters. During the broth removal/fresh medium charge cycle (about 1.5-2.5 hours), the fermentation pauses for 2-3 hours, i.e., without toluene, phosphate and acetate (growth carbon) feed addition, but with aeration at 0.5 VVM to maintain the viability of cells.

After the replenishment of fresh medium to the fermentor containing induced/active cells (450 kletts), the fermentation is resumed with an air-toluene rate of 750 cc/minute, and a 0.4 cc/minute of phosphate and acetate (aqueous solution of 10 weight percent acetic acid/0.114 weight percent $Na_2HPO_4$/0 218 weight percent $KH_2PO_4$) addition rate. The fed-batch mode of fermentation is continued for another 22 hours to a muconic acid concentration of 12 g/l in the fermentation broth, and the broth is then ultrafiltered in the previous manner.

The cell-free clear filtrate is adjusted to pH 1-1.5 with concentrated $H_2SO_4$. The precipitated muconic acid is filtered, washed and dried. The muconic acid is recovered as a white solid (purity 98.5+ percent based on acidity and C,H,O elemental analysis).

EXAMPLE IV

This Example illustrates a semi-continuous (repeated fed-batch) fermentation process for the production of muconic acid in accordance with a present invention embodiment.

A. Inoculum Preparation

The *Pseudomonas putida* Biotype A mutant strain (ATCC No. 31916), stored frozen (regular "NO" medium aqueous culture in polypropylene culture vial stored in liquid nitrogen), is thawed and transferred (1-1.5 ml) to a 250 ml shake flask containing 50 ml of regular "NO" medium with 20 mM of sodium acetate as the growth carbon source, and incubated at 30° C., 250 rpm for 16 hours to a turbidity of 90-110 klett units. Three shake flasks (150 ml inoculum) are inoculated aseptically to a 16 liter steam sterilizable fermentor containing 11.5 liter LP-2 medium (Table) with 20 mM of sodium acetate to start fermentation. The medium and the fermentor are sterilized for at least 30 minutes at 121° C. and 15 psig. After sterilization, the medium pH is adjusted to 6.9 with 5N KOH solution.

B. Enzyme Induction

After the inoculation, toluene is supplied to the fermentation medium in vapor phase via air (filter sterilized, inlet pressure 20 psig) stripping at an air-toluene vapor flow rate of 125 cc/minute. The fermentation temperature is controlled at 30° C., the pH at 6.9 with 10M $NH_4OH$ and 1M $H_2HO_4$ solutions and the dissolved oxygen at 30 to 90 percent saturation with 600 rpm agitation and 5-6 liter/minute aeration. Pluronic L61 polyol (BASF) is used as an antifoam agent.

As the turbidity of the fermentation medium reaches 60-90 klett units (about 8-10 hours after inoculation), an aqueous solution containing 20 weight percent acetic acid, 1 67 mole NaOH, 1.67 mole KOH, 0.227 weight percent $Na_2HPO_4$, 0.436 weight percent $KH_2PO_4$ is added to the fermentor medium at a rate of 0.4 ml/min. The air-toluene vapor rate is increased to 250 cc/minute, and then increased to 500-600 cc/minute as the broth turbidity reaches 500-600 kletts.

C. Semi-Continuous (Repeated Fed-Batch Fermentation)

The fed-batch mode of fermentation is continued for 25-30 hours (at 620 kletts) to a muconic acid product concentration of 15 g/l. The fermentation is stopped by turning off toluene and phosphate/acetate feeds. The fermentation broth is ultrafiltered to concentrate and to recycle the cells back to the fermentor. Fresh sterilized fermentation medium LP-2 is aseptically added to the fermentor to a total fermentation volume of 12 liters at a turbidity of 670 kletts After the replenishment of fresh medium, the fermentation is resumed by feeding the phosphate/acetate aqueous solution at 0.4 cc/minute and the air-toluene flow rate at 850 cc/minute. The fermentation is continued for another 16-18 hours to a muconic acid concentration of 17 g/l. The broth turbidity is 1000 kletts.

The fermentation broth is ultrafiltered to remove 10 liters of broth over a period of 2.5-3.0 hours. The fed-batch mode of fermentation is resumed (at 880 klett turbidity) after replenishment of fresh LP-2 medium. After 20 hours of fermentation, the broth turbidity reaches 1200 kletts, and the muconic acid concentration is 26 g/l. The air-toluene flow rate is increased to 1000 cc/minute, and 22.4 grams of $(NH_4)_2SO_4$ is added to the fermentor. The fermentation is continued for an additional 12 hours, and a muconic acid concentration of 31 g/l is achieved in the fermentation broth.

The broth is then ultrafiltered, and the cell-free clear filtrate is adjusted to pH 1-1.5 with concentrated $H_2SO_4$. The precipitated muconic acid is filtered, washed, dried and recovered as a white solid (purity 98.5+ percent based on acidity and C,H,O elemental analyses).

The above-described muconic acid concentration of 31 g/l (220 mM) produced by the present invention semi-continuous (repeated fed-batch) process is achieved with greater reactor efficiency than with either a standard batch procedure or a continuous mode of operation chemostat under comparable conditions. A continuous fermentation process is described in copending patent application Ser. No. 394,744, filed July 2, 1982, incorporated by reference.

The high muconic acid concentration is significant because it is achieved at a biocatalyst concentration which is 2-3 times greater than those usually employed in batch or continuous modes of fermentation. The cell concentration is 4.5-6.0 g/l as compared with 2.5-3.5 g/l in previously described batch or continuous fermentations. The average biocatalyst specific productivity is 0.3-0.5 g/g dry cell/hr with a STY (reactor productivity) of 1 g/l/hr. The capital and operating costs of the process are reduced because of higher productivity.

EXAMPLE V

This Example illustrates a semi-continuous (repeated fed-batch) fermentation process for the production of muconic acid in accordance with a present invention embodiment under optimized conditions.

A. Inoculum Preparation

A *Pseudomonas putida* mutant strain ATCC No. 31916, variant CEL 1014 culture (regular "NO" medium aqueous culture in polypropylene vial stored frozen in liquid nitrogen), is thawed and transferred (0.5-1.0 ml) to a 250 ml shake flask containing 50 ml of regular "NO" medium with 20 mM of sodium acetate as the growth carbon source, and is incubated at 30° C. (250 RPM) for 15-20 hours to an optical density of 90-100 klett units.

Six shake flasks (with a total of 300 ml inoculum) are inoculated aseptically into a 16-liter steam sterilizable fermentor containing 11.5 liters of sterilized LP-2 medium with 20 mM of sodium acetate to start fermentation. The medium and the fermentor are sterilized for at least 30 minutes at 121° C. and 15 psig. After sterilization, the medium pH is adjusted to 6.9 with 5N NaOH solution before inoculation.

B. Cell Growth/Enzyme Induction

After the inoculation, cells are allowed to grow for 8-10 hours to an optical density of 40-60 klett units. Toluene is then supplied to the fermentation medium in vapor phase via air (0.2 micron filter sterilized and inlet pressure 20 psig) stripping at an air-toluene vapor rate of 125 cc/minute. The toluene saturated air stream contains 3.7 mole percent toluene based on toluene vapor pressure at ambient 25° C. The fermentation temperature is controlled at 30° C.,the pH at 6.9 with 10M ammonium hydroxide and 1 M sulfuric acid solutions, and a dissolved oxygen level at 30-90 percent saturation wih 600 RPM agitation and 5-6 liter/minute aeration (or approximately 0.5 VVM, volume of air/volume of fermentation broth/minute, inlet air pressure 20 psig). Pluronic L61 polyol (BASF) is used as an anti-foam agent.

As the optical density of the fermentation medium reaches 60-90 klett units (about 10-12 hours after inoculation), an aqueous solution (Feed A, heat sterilized) containing 200 g/l acetic acid, 2.27 g/l $Na_2HPO_4$, 4.36 g/l $KH_2PO_4$, 93 g/l KOH and 66.6 g/l NaOH is added (pumped, FMI Piston Positive Displacement pump) to the fermentor medium at a rate of 0.4 ml/min (a fed-batch mode of fermentation). The air-toluene vapor rate is increased to 500 cc/minute and then increased to 1000 cc/minute as the broth optical density reaches 600 klett units. The air-toluene vapor rate is further increased to 1500 cc/minute as the broth optical density reaches 1000 klett units (24 hours after the start of the fed-batch fermentation).

A muconic acid product concentration of 28 g/l is formed in the fermentation broth and the average specific productivity or biocatalyst (cells) activity in the fermentor is calculated to be 0.84 g/gdw/hr (grams of muconic acid/grams of dry cell weight/hr). An aqueous solution (Feed B, heat sterilized) containing 53.9 g/l $(NH_4)_2SO_4$, 17.7 g/l $MgSO_4.7 H_2O$, 0.7 g/l $CaCl_2.2 H_2O$, and 0.4 g/l $FeSO_4.7 H_2O$ is added by FMI pump to the fermentor broth at a rate of 0.4 ml/minute.

C. Semi-Continuous (Repeated Fed-Batch) Fermentation

The fed-batch mode of fermentation is continued for another 26 hours and the broth optical density reaches 1900 klett units (or 6.6 g/l cell concentration). The muconic acid product concentration reaches a level of about 50 g/l. The biocatalyst activity is at a level of 0.2 g/gdw/hr because of product inhibition of the induced enzymes and product repression of cell synthesis of active enzymes.

The fermentation is stopped by turning off the toluene feed. The fermentation broth is ultrafiltered with a Romicon hollow tube "cross-flow" ultrafilter, to concentrate the cells for recycle to the fermentor. The ultrafilter has a polysulfone (hydrophobic) type ultra filtration membrane (PM-100, molecular weight cutoff 100,000). The cell-free permeate (about 9.5 liters) from the ultrafilter containing a high muconic acid concentration (about 50 g/l) is removed from the fermentor for product recovery.

The recycled concentrated cell fraction has a volume of 2-3 liters. Fresh sterilized fermentation medium LP-2 is aseptically added to the fermentor to a total volume of 12 liters, in which the muconic acid concentration is about 8 g/l. During the product broth removal/fresh medium charge period (about 1.5-2.5 hours), aeration at 0.5 VVM and Feeds A and B at 0.3 cc/minute are continued to maintain the viability of the cells.

After the replenishment of fresh medium to the fermentor broth containing cells at 1800 klett units, the biooxidation resumes with the introduction of toluene at an air/toluene flow rate of 1500 cc/minute. The fed-batch mode of fermentation is continued with the addition of 0.3 cc/minute of Feeds A and B. Three hours after the resumption of the fed-batch fermentation, the biocatalyst activity is regenerated to 0.36 g/gdw/hr. After fifteen hours, the biocatalyst activity increases to 0.72 g/gdw/hr and the muconic acid concentration reaches 32 g/l.

The repeated fed-batch fermentation is continued for another 12 hours and the muconic acid concentration reaches 45 g/l. The cell turbidity increases to 2600 klett units and the biocatalyst activity lowers to 0.24 g/gdw/hr.

The fermentation is then halted by turning off the toluene feed, and the fermentation medium is ultrafiltered with the Romicon hollow tube ultrafilter. The cell-free permeate with a muconic acid concentration of 45 g/l is removed from the fermentor/ultrafilter for product recovery by adjusting the cell-free permeate to pH 1-2 with concentrated sulfuric acid. The solubility of muconic acid at pH 1-2 fermentation broth is 0.02 weight percent. The precipitated muconic acid is filtered, washed, dried and recovered as a white solid (purity 99 percent based on acidity and C, H, 0 elemental analyses).

The fed-batch cycles are repeated for additional five cycles with approximately 24-27 hours for each fermentation/cell separation/recycle/permeate removal/fresh medium charge cycle. During the active production period (8-9 days), the toluene concentrations in the fermentation broth are maintained below 0.6 mM. The average reactor productivities are 1.8-2.0 g/l/hr (grams of muconic acid produced/liter of fermentation broth volume/hr). For each repeated fed-batch fermentation cycle a purge of approximately 1-3 percent of broth volume is effected to reduce any prospective accumulation of intracellular and extracellular inhibitory compounds.

TABLE
FERMENTATION MEDIA

| Chemicals (g/l) | Regular "NO" Medium | LP-1 Medium | LP-2 Medium |
|---|---|---|---|
| $Na_2HPO_4$ | 7.1 | 0.0426 | 0.0426 |
| $KH_2PO_4$ | 13.6 | 0.0817 | 0.0817 |
| $(NH_4)_2SO_4$ | 2.25 | 1.12 | 2.24 |
| $MgSO_4.7H_2O$ | 0.246 | 0.738 | 0.738 |
| $CaCl_2.2H_2O$ | 0.0147 | 0.0294 | 0.0294 |
| $FeSO_4.7H_2O$ | 0.00278 | 0.0167 | 0.0167 |

All chemical concentration are in g/l. Unless otherwise specified, the medium is prepared by adding appropriate growth carbon source in deionized water.

What is claimed is:

1. A semi-continuous bioconversion process operating in a fed-batch mode which comprises (1) continuously feeding a toluene non-growth substrate, an aqueous nutrient stream and molecular oxygen into a fermentation zone containing a Pseudomonad microorganism which bio-oxidizes the toluene by the ortho pathway to extracellular muconic acid product, and wherein the fermentation is conducted under nutrient-limitation conditions to stabilize cell population by restricting the growth of revertant cells; (2) maintaining the fermentation conditions until the concentration of the muconic acid product in the fermentation medium has reached a level of at least about 15 grams per liter of fermentation medium with essentially no product inhibition of enzymatic activity, then stopping the input of toluene and aqueous nutrient stream into the fermentation zone and continuing the input of molecular oxygen; (3) withdrawing the whole cell-containing fermentation broth from the fermentation zone and passing the withdrawn fermentation broth through a cross-flow membrane filtration zone, then recovering a whole cell-containing retentate stream and a cell-free product-containing permeate stream from the filtration zone and recycling the retentate stream to the fermentation zone; (4) charging the fermentation zone with a volume of fresh aqueous nutrient medium to replace the withdrawn volume of permeate fermentation broth, and resuming the fermentation conditions by recommensing the continuous feed of toluene and aqueous nutrient stream into the fermentation zone to produce muconic acid product up to a concentration of at least about 15 grams per liter of fermentation medium with essentially no product inhibition of enzymatic activity; (5) withdrawing the whole cell-containing fermentation broth from the fermentation zone and passing the with drawn fermentation broth through a cross-flow membrane filtration zone, then recovering a whole cell-containing retentate stream and a cell-free product-containing permeate stream from the filtration zone and recycling the retentate stream to the fermentation zone; and (6) recovering muconic acid product from the cell-free permeate streams, and optionally repeating the fed-batch cycle to produce additional muconic acid product.

2. A process in accordance with claim 1 wherein the fermentation is conducted under growth carbon-limited conditions to reduce catoblite repression.

3. A process in accordance with claim 1 wherein the fermentation is conducted under phosphorus-limited conditions to maximize cell enzyme induction and to stabilize cell population by restricitng the growth of revertant cells.

4. A process in accordance with claim 1 wherein approximately neutral pH conditions are maintained in the permentation medium during the bioconversion period.

5. A process in accordance with claim 1 wherein the non-growth substrate is catechol in place of toluene.

6. A process in accordance with claim 1 wherein the microorganism exhibits enzymatic bio-oxidation activity characteristic of Pseudomonas putida Biotype A strain ATCC 31916.

7. A process in accordance with claim 1 wherein the microorganism is Pseudomonas putida Biotype A strain ATCC 31916.

* * * * *